(12) United States Patent
Mandro et al.

(10) Patent No.: US 10,426,889 B2
(45) Date of Patent: *Oct. 1, 2019

(54) OPTICAL DISPLACEMENT SENSOR FOR INFUSION DEVICES

(71) Applicant: DEKA Products Limited Partnership, Manchester, NH (US)

(72) Inventors: Marc A. Mandro, Bow, NH (US); Larry B. Gray, Merrimack, NH (US)

(73) Assignee: DEKA PRODUCTS LIMITED PARTNERSHIP, Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/959,636

(22) Filed: Apr. 23, 2018

(65) Prior Publication Data

US 2018/0236167 A1 Aug. 23, 2018

Related U.S. Application Data

(63) Continuation of application No. 14/047,488, filed on Oct. 7, 2013, now Pat. No. 9,950,110, which is a continuation of application No. 12/395,862, filed on Mar. 2, 2009, now Pat. No. 8,552,361, which is a continuation of application No. 10/625,792, filed on Jul. 23, 2003, now Pat. No. 7,498,563.

(60) Provisional application No. 60/398,259, filed on Jul. 24, 2002.

(51) Int. Cl.
| | |
|---|---|
| *A61M 5/168* | (2006.01) |
| *A61M 5/145* | (2006.01) |
| *G01D 5/347* | (2006.01) |
| *A61M 5/315* | (2006.01) |

(52) U.S. Cl.
CPC ........ *A61M 5/16886* (2013.01); *A61M 5/145* (2013.01); *A61M 5/1456* (2013.01); *A61M 5/31525* (2013.01); *G01D 5/34746* (2013.01); *G01D 5/34776* (2013.01); *A61M 2205/3306* (2013.01); *A61M 2205/3379* (2013.01); *A61M 2205/6063* (2013.01)

(58) Field of Classification Search
CPC .............. A61M 5/16886; A61M 5/145; A61M 5/1456; A61M 5/31525; A61M 2205/3306; A61M 2205/3379; A61M 2205/6063; G01D 5/34746; G01D 5/34776

See application file for complete search history.

(56) References Cited

U.S. PATENT DOCUMENTS 8,552,361 B2 * 10/2013 Mandro ................ A61M 5/145 250/231.13

* cited by examiner

*Primary Examiner* — Georgia Y Epps
*Assistant Examiner* — Don J Williams
(74) *Attorney, Agent, or Firm* — McCormick, Paulding & Huber LLP

(57) ABSTRACT

An optical sensor for a delivery device having a piston that displaces a substance, such as a fluid, from a reservoir. The optical sensor has a light source and a detector array for imaging encoding features disposed along a plunger rod coupled to the piston. By virtue of the pattern of encoding features, an absolute position of the plunger rod relative to a fiducial position may be determined uniquely. Thus, the volume of fluid remaining in the reservoir, the rate of fluid delivery, and proper loading of the reservoir may be accurately ascertained. Additionally, the encoding may serve to uniquely identify a version of the reservoir which may be supplied in various versions corresponding, for example, to differing concentrations of a therapeutic agent to be dispensed.

20 Claims, 4 Drawing Sheets

OPTICAL DISPLACEMENT SENSOR FOR INFUSION DEVICES

CROSS REFERENCE TO RELATED APPLICATIONS

The present application is a continuation of U.S. application Ser. No. 14/047,488, filed Oct. 7, 2013, which is a continuation of U.S. application Ser. No. 12/395,862, filed Mar. 2, 2009, which is a continuation of U.S. application Ser. No. 10/625,792, filed Jul. 23, 2003, which claims priority to U.S. Provisional Application 60/398,259, filed Jul. 24, 2002, each of which is incorporated herein by reference in its entirety.

FIELD OF THE INVENTION

The present invention pertains to optical sensors for monitoring the source and/or amount of a substance, such as a medicinal agent, delivered by a delivery device.

BACKGROUND ART

Devices, such as pumps or manual pens, used for delivering substances, such as drugs or insulin, from a local reservoir into the body of a patient are prone to problems that may impede the intended delivery rate of the substance. Such problems may include clogging, mechanical sticking, or misidentification of the administered substance. It is thus desirable that the source of the delivered substance be positively identified by the delivery device, that the proper loading of the substance reservoir be verified, that the instantaneous volume of substance in the reservoir be ascertainable, and that both the rate of delivery and the precise volume of remaining liquid be accurately monitored. Prior use of an optical monitor for similar applications, such as described in U.S. Pat. No. 4,498,843 to Schneider, et al., has been limited to measurement of delivery rate. It is, furthermore, desirable that the aforesaid functions be provided both accurately and cost effectively.

SUMMARY OF THE INVENTION

In accordance with preferred embodiments of the invention, there is provided a displacement sensor for a dispensing device of the type that has a translating piston. The sensor has a plunger rod coupled to the piston, and the plunger rod has an encoded pattern of encoding features. A light source illuminates the encoded pattern and a detector array detects light from the illuminated encoded pattern and generates a detector signal such that, on the basis of the detected signal, a processor determines a displacement of the plunger rod relative to a fiducial reference position. The delivery rate of a substance dispensed by the device may also be determined. Additionally, the encoded pattern may serve to identify a reservoir type characterized, for example, by a distinct concentration of a therapeutic agent to be delivered by the dispensing device.

DETAILED DESCRIPTION OF SPECIFIC EMBODIMENTS

Figure 1:
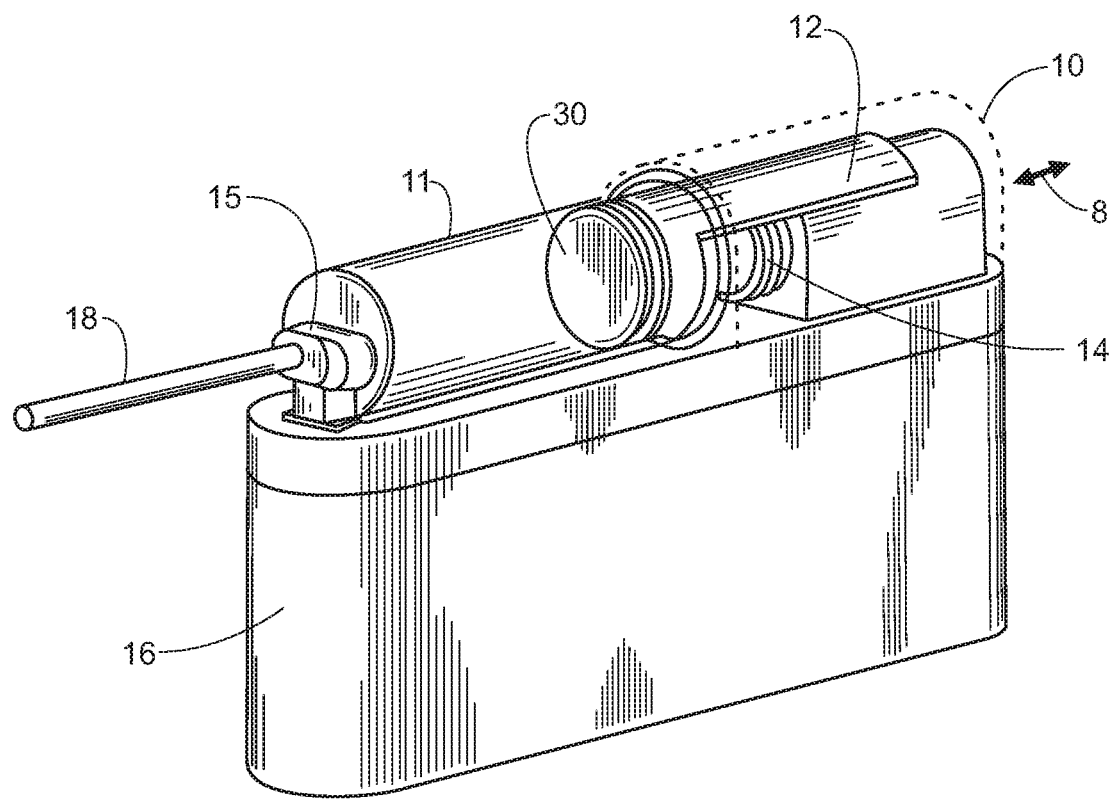
FIG. 1 shows the fundamental constituents of a prior art medical fluid pump.

Major components of a pump for delivering a therapeutic agent to the body of a patient are described with reference to FIG. 1. A medication reservoir 11, typically cylindrical in shape, is retained within a housing 16 and contains a liquid agent to be delivered to a patient via a delivery tube 18 and a hypodermic needle (not shown). The liquid agent contained within the reservoir is impelled out of the reservoir at a determined rate by linear motion of a piston 30 along a direction 8 coaxial with the axis of the reservoir. The piston is driven by a plunger rod 12 that is driven, in turn, at a prescribed rate, by a motor (not visible) coupled to a screw drive 14 via a gear reduction drive. It is to be understood that the present invention may advantageously be applied for delivery devices other than pumps, such as insulin pens, as well as for the delivery of various fluids or other substances that may be medicating agents or other substances. The description of a pump and in terms of delivery of a therapeutic agent to a patient is without limitation and by way of example only. Embodiments of the present invention may also advantageously be applied, for example, for delivery of purification agents into a water supply. The fluid to be delivered is typically a liquid, however the delivery of other substances is also within the scope of the present invention as described herein and as claimed in any appended claims.

The rate at which the pump motor is driven in order to impel the piston to deliver the liquid agent at a prescribed rate is governed by a processor on the basis of the cross section of the reservoir (i.e., the volume of agent expelled per unit linear motion of the piston) and the concentration of agent within the fluid contained in the reservoir.

In accordance with preferred embodiments of the present invention, an optical linear encoder is used to determine both the absolute position and rate of motion of the plunger rod. Additionally, since the reservoir and piston may be supplied to the user as an integral unit, additional information may be encoded on the plunger rod, as described in greater detail below.

It is desirable, in particular, that four functionalities be provided by a sensor used in conjunction with fluid delivery:
 a. monitoring delivery accuracy;
 b. identifying a characterizing feature of the reservoir (such as to its contents);
 c. determining the volume of fluid remaining in the reservoir; and
 d. verifying proper loading of the reservoir.

It is particularly advantageous if, as in accordance with a preferred embodiment of the present invention, all of the above functionalities may be provided by a single sensor.

If, as in preferred embodiments of the present invention, the reservoir identification is associated with the concentration in the fluid of a drug to be delivered by the infusion device, then a programmed dose may be converted into a linear distance.

Figure 2:
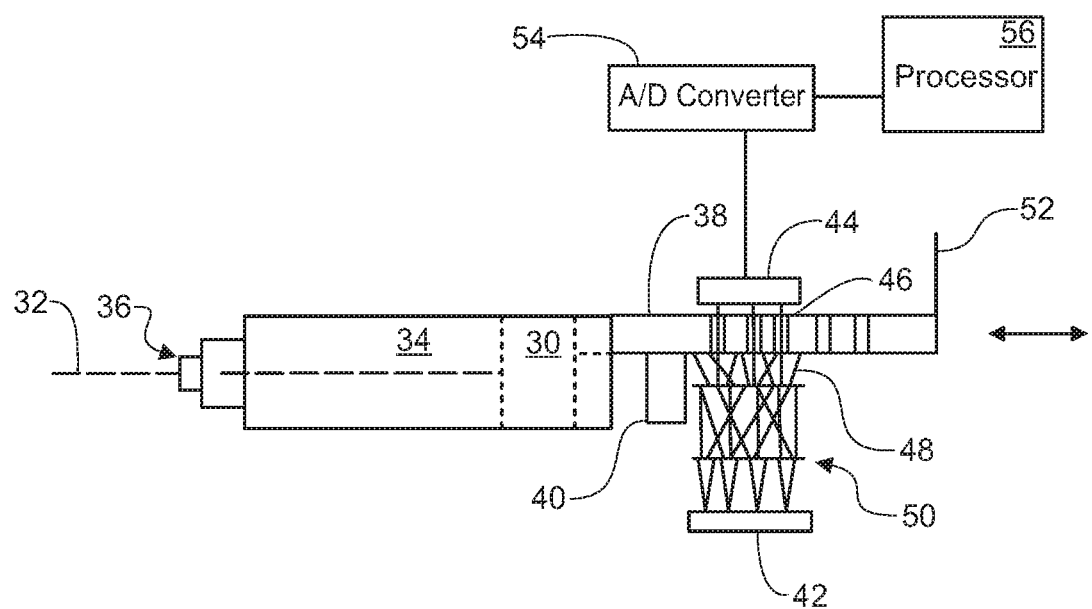
FIG. 2 is a schematic depiction of an optical linear encoder for delivery of a liquid agent in accordance with preferred embodiments of the present invention.

In preferred embodiments, transmission-type encoding is employed, however, any analogous reflection-type encoding is within the scope of the invention. Referring to FIG. 2, piston 30 is driven along axis 32 so as to impel the liquid contents of reservoir 34 out orifice 36. Piston 30 is propelled by plunger rod 38, which advances as lead screw 40 is rotated. In the preferred embodiments of transmission-type encoding, a light source 42 and detector 44 are disposed on opposite sides of plunger rod 38. As used herein, the term "detector" may refer, as the context demands, to an array of detectors. The detector or detector array may also be referred to, herein, as an "image sensor" or an "image array." The term "detector assembly" may refer to a detector or array of detectors along with associated preamplification and signal-conditioning electronics. Plunger rod 38 is encoded, in such embodiments, by features 46 that may be recognized by detector 44.

In accordance with one embodiment of the invention, encoding features 46 are slots orthogonal to the axis of travel 32 of the piston are scored into plunger rod 38. In alternate embodiments, round (or otherwise shaped) holes, or slots parallel to axis 32, wedges, or other light-transmitting features may be employed, all the above provided solely for purposes of example and without limitation. Slots 46 or other optically transmissive features may be fully optically transmissive or may, alternatively, modulate the some detectable characteristic of light (designated by dashed lines 48) transmitted between source 42 and detector 44. Transmissive features 46 may thus employ filters (of neutral density or otherwise), thereby modulating the intensity and/or spectral characteristics of the transmitted light, or may employ polarizers or retardation plates, thereby modulating the polarization or phase of the transmitted light. All such techniques for encoding transmitted light are within the scope of the present invention as described herein and as claimed in any appended claims.

In accordance with preferred embodiments of the present invention, detector 44 advantageously spans merely a portion of the region of plunger rod, as described in greater detail below, however any relative sizes of the detector 44 and plunger rod 38 are within the scope of the present invention.

The path of light from light source 42 to detector 44 may be one of direct transmission through plunger rod 38 as shown. Alternatively, encoding 46 may be detected in reflection by suitable placement of detector 44 on the same side of plunger rod 38 as light source 42. Light source 42 may be an array of light-emitting-diodes (LEDs), in which case diffuser 50 may be employed. Other sources of diffuse light, such as electro-luminescent light sources may also be employed. Diffuser 50 may include multiple diffusion stages, as shown. Illumination may also be provided by undiffused light. Illumination may be transmitted through encoding 46 directly onto detector 44, as shown, or, in other embodiments of the invention, a reflective light path or transfer of illumination pattern via optical fibers or other light pipes may be employed. Intervening optics such as a lens, microchannel plate, etc., may also be provided within the optical path, within the scope of the present invention.

Figure 3:
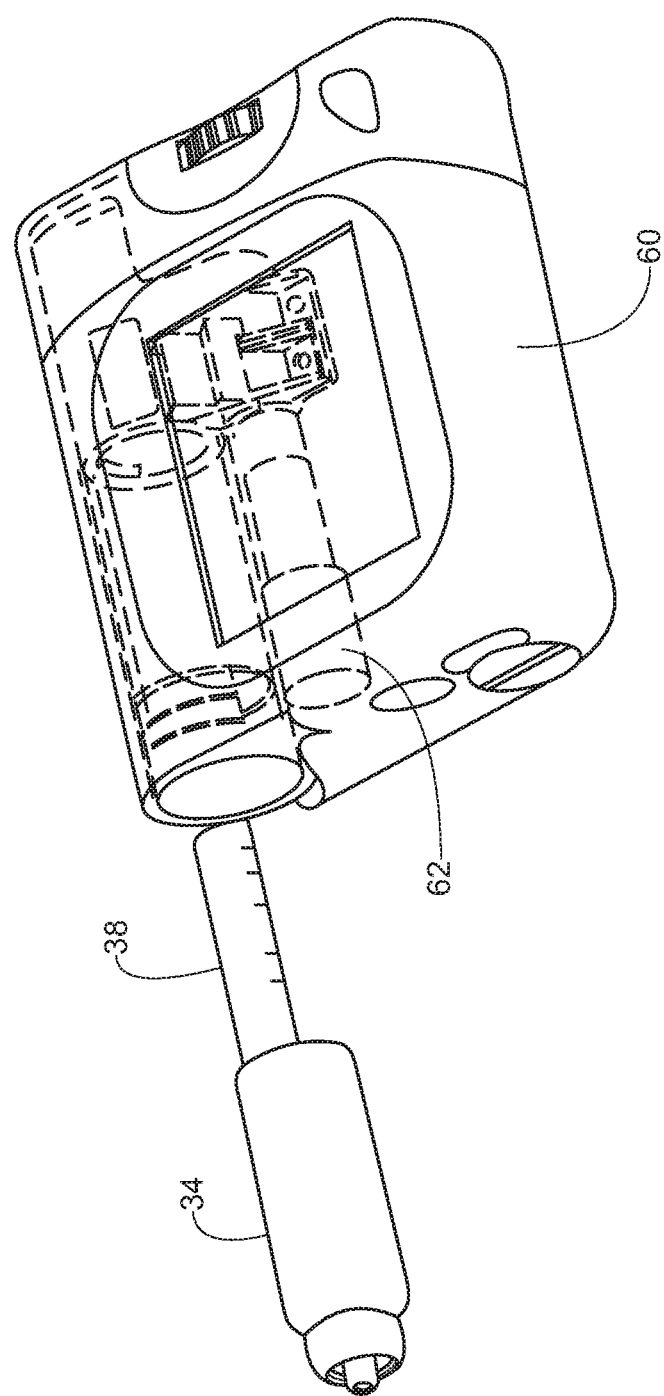
FIG. 3 is a perspective view of a medical fluid pump including an optical linear encoder in accordance with an embodiment of the present invention.
Figure 4:
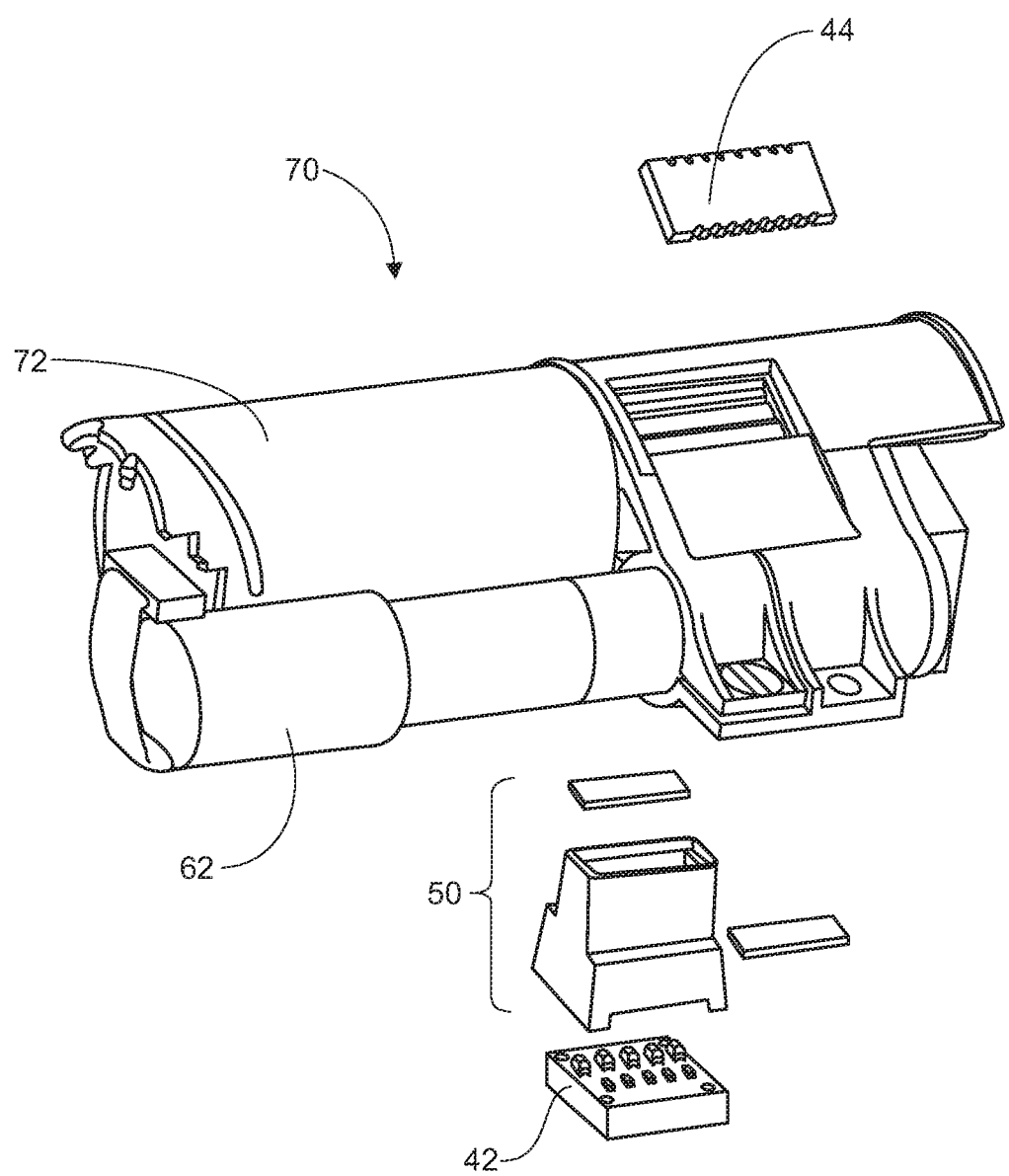
FIG. 4 is an exploded view of an embodiment of an optical linear encoder in accordance with the invention as applied to a medical fluid pump.

A housing 60 for embodying the substance dispenser components of FIG. 2 is shown in perspective view in FIG. 3. Motor drive 62 is hidden from view but shown as a dashed component. Reservoir 34, with plunger rod 38 in extension therefrom, is shown prior to insertion into the housing. The exploded view of FIG. 4 shows drive module 70, containing drive motor 62 and reservoir barrel 72, light source module 42, diffuser 50, detector 44

Detector 44 may be comprised of multiple detector resolving elements, and may be realized as a CMOS linear image sensor, for example, or a charge-coupled device (CCD) array, for another example. Many formats may be employed advantageously. Within the scope of the present invention, the detector elements may be linearly or two-dimensionally arrayed, and such arrays may be realized, if design considerations so require, by both linear and lateral stacking of detector arrays.

The image formed on detector 44 is analyzed, by directing the output signal of detector 44, via analog-to-digital converter 54, to processor 56, in accordance with various algorithms to be discussed in detail below. Pixel size and number are optimized with respect to resolution and resources demanded of processor 56.

By means of employing an encoding pattern that does not repeat, positioning of the moveable plunger rod with respect to the fixed optical assembly (taken to comprise both the illuminating and detecting optics) may advantageously be determined absolutely. Alternatively, the slot pattern or other encoding pattern may be repeated one or more times, thereby allowing translation to be encoded over large travel distances. In embodiments wherein the encoding pattern defines a non-unique current position of the plunger rod, plunger rod 38 may be driven to a fiducial position 52, such as a limit stop, in order to establish a reference from which to count repeats and to establish an absolute present position of the plunger rod relative to the fiducial position.

In preferred embodiments of the invention, detector 44 is realized as a 512-pixel linear array, with pixel resolution of approximately 16 .mu.m. Detector 44 is positioned along and parallel to the line of travel of plunger rod 38, beginning substantially at the end of lead screw 40. Particularly when focusing optics are not employed, it is preferred that detector 44 should be positioned in close proximity to plunger rod 38.

In a preferred embodiment of the invention, the spacing of plunger rod slots 46 is chosen in such a manner that any two adjacent spaces form a unique sequence. Additionally, the sum of the lengths of any two spaces is always greater than the distance between any two adjacent slots, thus, in case a slot becomes unintentionally blocked, the anomaly may be detected and not mistaken for another absolute position. Additionally, it is provided that either three or more slots are visible to the image sensor at any one time, or else the end of the rod and at least one slot are visible to the image sensor at any given time.

The three versions of slot spacings, given in inches in Table I, meet the preferred criteria discussed in the foregoing paragraph. The spacing of any two adjacent spaces may be coded to uniquely define a version of the reservoir, so that different concentrations of medicinal agent may be supplied and distinguished. Characteristics of the reservoir version that may be identified in this manner include, without limitation, the inner diameter of the reservoir, and the composition (plastic or glass, for example) of the wall of the reservoir. Additionally, the distance between the end of the plunger rod and the last slot may uniquely identify a reservoir version, so that, in case no more than one slot is within the field of view of the image sensor, the reservoir version may be uniquely identified.

TABLE I

| | Slot To Slot Distance (inches) | | | | | | | | | |
|---|---|---|---|---|---|---|---|---|---|---|
| Version | Slot 1 to Slot 2 | Slot 2 to Slot 3 | Slot 3 to Slot 4 | Slot 4 to Slot 5 | Slot 5 to Slot 6 | Slot 6 to Slot 7 | Slot 7 to Slot 8 | Slot 8 to Slot 9 | Slot 9 to Slot 10 | Slot 10 to end |
| #1 | 0.084 | 0.096 | 0.084 | 0.084 | 0.060 | 0.096 | 0.108 | 0.060 | 0.060 | 0.110 |
| #2 | 0.072 | 0.060 | 0.072 | 0.096 | 0.096 | 0.072 | 0.084 | 0.108 | 0.072 | 0.095 |
| #3 | 0.060 | 0.108 | 0.096 | 0.060 | 0.084 | 0.072 | 0.072 | 0.108 | 0.084 | 0.080 |

To create an image, all pixels of detector 44 are reset. Then light source 42 is flashed such that light is emitted for a specified duration of time. Variable-duration exposure times may be employed, such that longer times are used when slots are being viewed, whereas shorter times are used when the end of the plunger rod is being viewed. Exposure times of 5 ms for slots and 0.7 ms for the end of the rod have been found to be satisfactory. The signal from detector 44 is read, with values for each pixel stored by processor 56 in an array and interpreted using one or more algorithms.

In the embodiment to which Table I refers, there is a small portion of the travel where only two slots are visible (9 and 10) as well as the end of the rod. The normal means of identifying the syringe using two adjacent spaces cannot be used since only a single spacing is available. The alternate means of identifying the syringe using the distance between the end of rod and the last slot cannot be used because the end is too close to the edge of view to be detected using the sliding window algorithm. Thus a third means of identifying the syringe is used when only two slots are visible and the end of the rod position cannot be measured but is visible. This third method relies on a unique slot-9-to-slot-10 spacing.

In accordance with one exposure procedure, the light is left on. Then, the detector reads and resets each pixel in sequence at a specific clock rate. The array is then read twice, the first read serving to reset the pixels. The second read of each pixel thus occurs "n" times the clock period since that pixel was reset.

In a preferred mode of operation, measurements of plunger rod position are made once per basal step of the piston, during delivery of a bolus, and during priming. In between measurements, image sensor power may be removed, since the position determination is absolute.

In accordance with embodiments of the invention, various algorithms may be employed in order to detect the position of transmitted light peaks to within specified resolution. One Peak Detection Algorithm employs a sliding window split into two equal halves. The values of pixels in each half are summed, and the sums subtracted from each other. The difference between the signals in the two halves is calculated for all possible positions of the sliding window, giving a measure of the slope of the intensity curve. As zeroes occur at local extrema, whether peaks or valleys, the sign of the difference value as the zero point is approached is used to distinguish between these two cases. Other peak and edge identifying algorithms are within the scope of the present invention. Movement of the peaks may be used to track the accuracy of plunger rod movement and thus delivery of the liquid agent being driven out of the reservoir.

In accordance with further embodiments of the invention, the spacing between slots can be resolved to finer increments than the pitch of detector 44 by storing the A/D pixel values in a software array with power-of-2 more elements than the sensor array. For example, resolution would be increased eightfold if a 512 pixel image was stored in a 4096 element software array. This is done by storing the $1^{st}$ sensor array value in each of the $1^{st}$ eight software array elements. The $2^{nd}$ sensor array value is stored in each of the next eight software array elements, and so on.

Alternatively, by reading every $n^{th}$ pixel, where n is a power of 2, and storing these values in a software array with the same number of elements as the sensor array, image read times can be decreased without adversely affecting the slot to slot measurement resolution.

Having thus described various illustrative embodiments of the present invention, some of its advantages and optional features, it will be apparent that such embodiments are presented by way of example only and are not by way of limitation. It is to be understood that the teachings of the present invention may be applied to the metered delivery of fluids for other applications, such as the delivery of chemicals to a supply of potable water, to name merely a single example. Those skilled in the art could readily devise alternations and improvements on these embodiments, as well as additional embodiments, without departing from the spirit and scope of the invention. All such modifications are within the scope of the invention as claimed.

What is claimed is:

1. A medical fluid dispensing apparatus for pumping an infusible medical fluid to the body of a patient, the medical fluid dispensing apparatus comprising:
   a piston having an encoded pattern associated therewith; and
   an optical sensor, wherein the optical sensor is configured to determine the position of the piston, relative to a fiducial position based on the encoded pattern during delivery regardless of whether the encoded pattern associated with the piston repeats.

2. The apparatus of claim 1, further comprising a reservoir and a motor, wherein the piston is driven by the motor, at a prescribed rate, to impel the medical fluid out of the reservoir.

3. The apparatus of claim 1 further comprising a plunger rod coupled to the piston, the plunger rod bearing the encoded pattern, the encoded pattern including at least one encoding feature, wherein the encoding feature include at least one optically transmissive feature.

4. The apparatus of claim 3 further comprising an illumination source, the illumination source located wherein light from the illumination source is transmitted to the at least one optically transmissive feature.

5. The apparatus of claim 3 further comprising at least one detector for detecting light transmitted to the at least one encoding feature.

6. The apparatus of claim 5 wherein the at least one encoding feature is a slot scored into the plunger rod.

7. The apparatus of claim 5 wherein the at least one encoding feature is an aperture.

8. The apparatus of claim 1 further comprising a plunger rod coupled to the piston, the plunger rod bearing the encoded pattern, the encoded pattern including encoding features, wherein the encoding features comprising a plurality of optically transmissive features.

9. The apparatus of claim 8 wherein the spacing of the encoding features from one another defines spaces between such that any two adjacent spaces form a unique sequence.

10. The apparatus of claim 1 further comprising a plunger rod coupled to the piston, the plunger rod bearing an encoded pattern of at least one encoding feature, wherein the encoding feature include at least one reflective feature.

11. The apparatus of claim 10 further comprising an illumination source, the illumination source located wherein light from the illumination source is transmitted to the at least one reflective feature.

12. The apparatus of claim 10 further comprising at least one detector for detecting light reflected by the at least one encoding feature.

13. The apparatus of claim 1 further comprising a plunger rod coupled to the piston, the plunger rod bearing the encoded pattern, the encoded pattern including encoding features, wherein the encoding features comprising a plurality of reflective features.

14. The apparatus of claim 13 wherein the spacing of the encoding features from one another defines spaces between such that any two adjacent spaces form a unique sequence.

15. A medical fluid dispensing apparatus for pumping an infusible medical fluid to the body of a patient, the medical fluid dispensing apparatus comprising:

a piston;

a plunger rod coupled to the piston, the plunger rod bearing an encoded pattern of at least one encoding feature, wherein the encoding feature includes at least one reflective feature; and an optical sensor, wherein the optical sensor is configured to determine the position of the piston, relative to a fiducial position, based on the encoded pattern during delivery regardless of whether the encoded pattern includes unique or non-unique encoding features.

16. The apparatus of claim 15, further comprising a reservoir and a motor, wherein the piston is driven by the motor, at a prescribed rate, to impel the medical fluid out of the reservoir.

17. The apparatus of claim 15 further comprising an illumination source, the illumination source located wherein light from the illumination source is transmitted to the at least one reflective feature.

18. The apparatus of claim 17 further comprising at least one detector for detecting light reflected by the at least one encoding feature.

19. The apparatus of claim 15 further comprising wherein the plunger rod comprising a plurality of reflective features.

20. The apparatus of claim 19 wherein the spacing of the encoding features from one another defines spaces between such that any two adjacent spaces form a unique sequence.

* * * * *